United States Patent [19]

Baggiolini et al.

[11] Patent Number: 4,613,594

[45] Date of Patent: Sep. 23, 1986

[54] FLUORINATED VITAMIN D$_3$ COMPOUNDS

[75] Inventors: Enrico Baggiolini, North Caldwell; Giacomo Pizzolato, Glen Ridge; Milan Uskokovic, Upper Montclair; Gary Truitt, Passaic, all of N.J.

[73] Assignee: Hoffmann-La Roche Inc., Nutley, N.J.

[21] Appl. No.: 672,059

[22] Filed: Nov. 16, 1984

[51] Int. Cl.$^4$ .............................................. C07J 9/00
[52] U.S. Cl. ................................... 514/167; 260/397.2
[58] Field of Search ..................... 260/397.2; 514/167; 568/664, 374, 819

[56] References Cited

U.S. PATENT DOCUMENTS

| | | | |
|---|---|---|---|
| 4,248,791 | 2/1981 | DeLuca et al. | 260/397.2 |
| 4,358,406 | 11/1982 | DeLuca et al. | 260/397.2 |
| 4,391,802 | 7/1983 | Suda et al. | 260/397.2 |
| 4,411,833 | 10/1983 | De Luca et al. | 260/397.2 |
| 4,505,906 | 3/1985 | De Luca et al. | 260/397.2 |

OTHER PUBLICATIONS

Dokoh, S. et al. The Ovary: A Target Organ for 1, 25-dihydroxyvitamin D$_3$, *Endocrinology* 112: 200-206, 1983.
Murao, S. Control of Macrophage Cell Differentiation in Human Promyelocytic HL-60 Leukemia Cells by 1,25-dihydroxyvitamin D$_3$ and phorbol-12-myristate-13-acetate, *Cancer Res.* 43 (8): 4989-4996, 1983.
Reitsma, P. et al. Vitamin D$_3$ Regulates c-myc Oncogene Expression in HL-60 Leukemic Cells, *J. Cell Biol.* 97 (5): 347a, 1983.
Rigby, W. F. C. et al. 1,25-dihydroxyvitamin D$_3$ Induces Granulocytic Differentiation and Myeloid Specific Antigens in the HL-60 Promyelocytic Leukemia Cell Line, *Blood* 62 (5): 153a, 1983.
Olsson, I., and Lund, U. Induction of Differentiation of the Human Histiocytic Lymphoma Cell Line U937 by 1α, 25-dihydroxycholeciferol, *Cancer Res.* 43 (12) 5862-5867, 1983.
Eisman, J. A. et al. 1,25-dihydroxyvitamin-D Receptor in Breast Cancer Cells, *Lancet*, Dec. 22/29: 1335-1336, 1979.
Frampton, R. J. et al. Presence of 1,25-dihydroxyvitamin D$_3$ Receptors in Established Human Cancer Cell Lines in Culture, *Cancer Res.* 42: 1116-1119, 1982.
Colston, K. et al. 1,25-dihydroxyvitamin D$_3$ Receptors in Human Epithelial Cancer Cell Lines, *Cancer Res.* 42: 856-859, 1982.
Sher, E. et al. Whole Cell Uptake and Nuclear Localization of 1,25-dihydroxycholecalciferol by Breast Cancer Cells (T47D) in Culture, *Biochem. J.* 200: 315-230, 1981.
Frampton, R. J. et al. Inhibition of Human Cancer Cell Growth by 1,25-dihydroxyvitamin D$_3$ Metabolites, *Cancer Res.* 43: 4443-4447, 1983.
Shiina, Y. et al. Biological Activity of 24,24-difluoro-1α,25-dihydroxyvitamin D$_3$ and 1α,25-dihydroxyvitamin D$_3$-26,23-lactone in Inducing Differentiation of Human Myeloid Leukemia Cells, *Arch. Biochem. Biophys.* 220: 90-94, 1983.
Abe, E. et al. Differentiation of Mouse Myeloid Leukemia Cells Induced by 1α,25-dihydroxyvitamin D$_3$, *Proc. Natl. Acad. Sci. USA* 78: 4990-4994, 1981.
McCarthy, D. 1α,25-dihydroxyvitamin D$_3$ Causes Granulocytes from Patients with Chronic Granulocytic Leukemia to Differentiate into Monocytes-macrophages: This Effect is Mediated by a Protein Receptor, *Exp. Hematol.* 11 (Suppl. 14): 200, 1983.
Honma, Y. et al. 1α,25-dihydroxyvitamin D$_3$ and 1α-hydroxy Vitamin D$_3$ Prolong Survival Time of Mice Inoculated with Myeloid Leukemia Cells, *Proc. Natl. Acad. Sci. USA* 80: 201-204, 1983.
Sato, T. et al. Antitumor Effect of 1α-hydroxyvitamin D$_3$, *Tohoku J. Exp. Med.* 138: 445-446, 1982.
McCarthy, D. M. et al. A Role for 1,25-dihydroxyvitamin D$_3$ in Control of Bone Marrow-collagen Deposition? *Lancet* Jan. 14: 78-80, 1984.
Koeffler et al., "Induction of Macrophage Differentiation of Human Normal and Leukemic Myeloid Stem Cells by 1,25-Dihydroxyvitamin D$_3$ and its Fluorinated Analogues[1]", *Cancer Research* 44, 5624-5628, Dec. 1984.

*Primary Examiner*—Elbert L. Roberts
*Attorney, Agent, or Firm*—Jon S. Saxe; Bernard S. Leon; Matthew Boxer

[57] ABSTRACT

Novel hexafluoro-cholecalciferol compounds and processes for preparing such compounds are disclosed. Intermediates utilized in the preparation of such compounds and pharmaceutical preparations containing these compounds are also disclosed.

14 Claims, No Drawings

FLUORINATED VITAMIN $D_3$ COMPOUNDS

BACKGROUND OF THE INVENTION

It has been known in the art to introduce fluorines on the 26 and 27 carbon atom in certain vitamin $D_3$ metabolites in order to enhance vitamin D like activity. Thus, for example, U.S. Pat. No. 4,358,406 describes 26,26,26,27,27,27-hexafluoro-1α,25-dihydroxycholecalciferols which are indicated to have greater vitamin D-like activity compared to the analogous unfluorinated compounds. The compounds of the patent are indicated to be useful in human and veterinary medicine for treatment of calcium and phosphorus deficiency or imbalance. These compounds are thus useful in the treatment of hypoparathyroidism, pseudohypoparathyroidism, renal osteodystrophy, osteoporosis and other bone disorders symptomatic of calcium and phosphorus imbalance. Veterinary applications include, for example, treatment of milk fever in cattle, leg weakness in turkeys, chickens and other domestic animals. Indicated therapeutic dosages for the above indications ranged from 0.1 to 2.5 micrograms/day orally or parenterally.

In U.S. Pat. No. 4,298,791 there is disclosed 25-hydroxy-26,26,26,27,27,27-hexafluorocholecalciferol. This compound is indicated to have excellent vitamin $D_3$-like activity as measured by ability to stimulate calcium transport in the intestine and to mobilize calcium from bone and in its antirachitic activity. Thus the compound is useful in treatment of disease resulting from calcium metabolism disorder.

SUMMARY OF THE INVENTION

The present invention relates to novel hexafluorocholecalciferol derivatives that exhibit enhanced vitamin $D_3$-like activity. More particularly the present invention relates to $\Delta^{22}$ and $\Delta^{23}$26,26,26,27,27,27-hexafluoro-1α,25-dihydroxy-cholecalciferols which are unexpectedly more potent than other vitamin $D_3$ derivatives and analogs in assays which predict vitamin $D_3$-like and anti-proliferative activities. Further aspects of the invention relate to the processes and novel intermediates utilized to prepare the desired end products and pharmaceutical preparations containing the biologically active end products.

DESCRIPTION OF THE INVENTION

The novel $\Delta^{22}$ and $\Delta^{23}$-compounds of the present invention are conveniently prepared by synthesis from the novel indene sulfone intermediate of the structure:

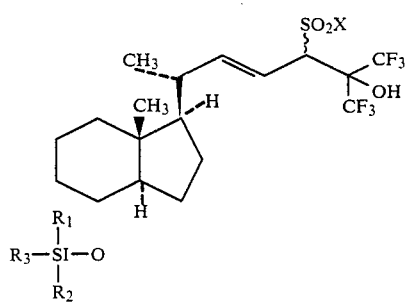

where X is aryl, preferably phenyl and $R_1$, $R_2$, $R_3$ each independently are lower alkyl, aryl or aralkyl, preferably, (1,1-dimethylethyl) and $R_1$ and $R_3$ each are methyl.

In such synthesis the compounds of formula I above as an epimeric mixture of arylsulfonyls at the 4 position are dearylsulfonylated using an alkali metal biphosphate followed by treatment with an alkali metal amalgam. This reaction is conveniently carried out in a suitable inert organic solvent or solvent mixture such as a lower alkanol or cyclic ether or preferably mixtures thereof. Preferred reactants include dipotassium hydrogen phosphate and sodium analgam, while preferred solvents include methanol, tetrahydrofuran and a mixture of methanol and tetrahydrofuran most preferable a 1:1 (v/v) mixture.

The initial reaction step involving treatment with the biphosphate is conveniently carried out at ambient conditions whereas the alkali metal amalgam addition is carried with cooling, preferably at temperatures below 0° C., most preferably at about −20° C.

Purification of the reaction products is carried out using chromatographic procedures known per se. Thus, in preferred embodiments a combination of silica column chromatography, treatment with a cation exchange resin and finally a selective silica column chromatography step provides the following two reaction products (II-A and II-B) in purified and separated form:

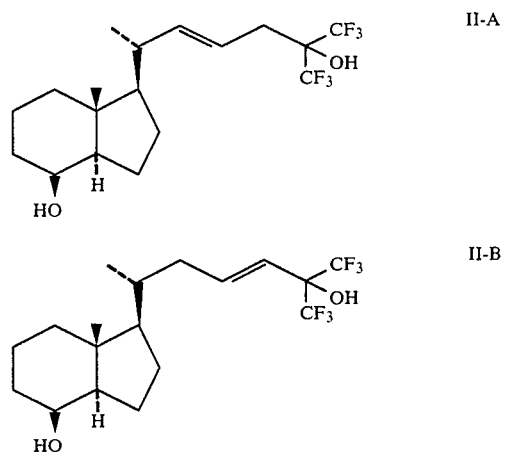

As seen from the structures of II-A and II-B above, the aforesaid procedure also removes the (1,1-dimethylethyl)dimethylsilyl protecting group from the ring hydroxy moiety. Compound II-A serves as the intermediate for the $\Delta^{22}$ end product of the invention whereas compound II-B serves as the intermediate for the $\Delta^{23}$ end product. Thus, in succeeding steps A in the side chain will indicate unsaturation in the side chain for the series based on intermediate II-A while B in the side chain will indicate unsaturation in the side chain for the series based on intermediate II-B.

The next step in the synthesis involves oxidation of the ring hydroxyl group using a chemical oxidation agent. Suitable oxidation agents for this purpose include chromate salts particularly with basic organic amines such as for example pyridinium halochromates, preferably pyridinium chlorochromate. The reaction is carried out under ambient conditions of temperature and pressure using an inert solvent. Suitable inert solvents include the halogenated alkanes, preferably a chloroalkane such as methylene chloride. There is thus obtained ketones of the formula

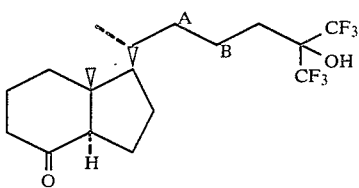

Ketones of formula III-A or III-B are treated with a trimethylsilylization agent to introduce a trimethylsilyl protecting group on the side chain hydroxy. A preferred reagent for this purpose is trimethylsilylimidazole. The reaction is conveniently carried out at ambient temperature preferably under an inert atmosphere, e.g. argon.

The resulting protected compounds of the formula:

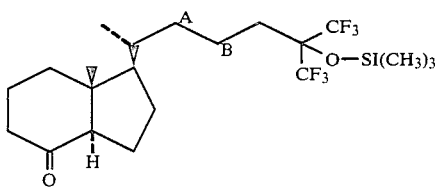

are reacted with [3S-(3α,5β,Z)]-2-(2-methylene-3,5-bis[(1,1-dimethylethyl)dimethylsilyloxy]cyclohexylidene]ethyldiphenyl phosphine oxide to yield the desired end products of the invention:

(A) 26,26,26,27,27,27-hexafluoro-1α,25-dihydroxy-$\Delta^{22}$-cholecalciferol (B) 26,26,26,27,27,27-hexafluoro-1α,25-dihydroxy-$\Delta^{23}$-cholecalciferol.

The above reaction is carried out at reduced temperatures e.g. below $-50°$ C., most preferably at about $-78°$ C. using an inert atmosphere such as for example an argon atmosphere. A suitable inert solvent may be employed in carrying of this reaction, for example, a cyclic ether, most preferably tetrahydrofuran. It is desirable to convert the phosphine oxide to a corresponding carbanion to facilitate the desired reaction. This is readily accomplished by initially treating the phosphine oxide with an alkyl lithium such as preferably n-butyl lithium in an inert solvent such as a lower alkane, e.g. hexane at reduced temperatures as above.

The final products of the invention can be purified by procedures known per se such as, for example, by use of silica gel chromatography.

The novel starting materials of formula I used in the above described synthesis are readily obtainable from known compounds available in the art. Thus, for example, [1R-[1β,[αS*,βS*],3aα,4aβ,7aβ]]-octahydro-β,7a-dimethyl-4-[[(1,1-dimethylethyl)dimethylsilyl]oxy]-α-ethenyl-1H-indene-1-ethanol can be converted into [1R-[1β(R*),3aα,4β,7aβ]]-1-(4-chloro-1-methyl-2-butenyl)-octahydro-4-[[(1,1-dimethylethyl)dimethylsilyl]-oxy]-7a-methyl-1H-indene by treatment with thionyl chloride followed by pyridine. The resulting allylic chloride is then reacted with an aryl sulfinic acid salt, preferably benzene sulfinic acid sodium salt to yield the corresponding 4-arylsulfonyl compound, e.g., [1R-[1β(R*),3aα,4β,7aβ]-1-[4-phenylsulfonyl)-1-methyl-2-butenyl)octahydro-4-[[(1,1-dimethylethyl)dimethylsilyl]oxy]-7a-methyl-1H-indene. The completion of the side-chain to produce a compound of formula I is accomplished by reacting the carbanion of the aforesaid sulfonyl compound, formed by treatment with n-butyl lithium or lithium diisopropylamide, with hexafluoroacetone.

The specific details of each of the reaction steps used in producing the intermediates of formula I according to the synthetic steps outlined above are set forth in the accompanying Examples below.

The $\Delta^{22}$- and $\Delta^{23}$-26,25,26,27,27,27-hexafluoro-1α,25-dihydroxycholecaliferols of the present invention can be administered in dosages that are in the range of about 0.10–3.0 micrograms/per day for the treatment of such disease states as osteoporosis, osteodystrophy, steroid induced osteopenia, hypoparathyroidism, hypophosphatemic rickets and hypophosphatemic osteomalacia which are characterized by lower than normal levels of endogeneously produced 1,25-dihydroxycholecalciferol. The compounds of the invention are also powerful specific inducers of cell differention and inhibitors of cell proliferation. Thus, such compounds are useful agents in the treatment of proliferative disease states such as leukemia. Preferable dosage ranges are 0.25–2.0 micrograms per day for the treatment of the aforementioned disease states. The compounds of the invention can be administered orally, subcutaneously, intramuscularly, intravenously, intraperitoneally or topically.

The aforesaid $\Delta^{22}$- and $\Delta^{23}$-products can be formulated into compositions such as tablets, capsules, and the like, or elixers for oral administration, or in sterile solutions or suspensions for parenteral administration for the treatment of the aforementioned disease states. About 0.10–3.0 micrograms, preferably 0.25–2.0 micrograms, is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as calcium phosphate; a disintegrating agent such as corn starch, potato starch, algenic acid, and the like; a lubricant such as magnesium stearate, sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

The above $\Delta^{22}$- and $\Delta^{23}$-products of the invention can be administered for the treatment of milk fever in pregnant ruminant animals prior to parturation in dosages in the range of 100–1500 micrograms/day using conventional formulations.

Sterile compositions for injection and/or topical administration can be formulated according to conventional practice by dissolving or suspending the respective $\Delta^{22}$- or $\Delta^{23}$-product in a vehicle such as a 10–20% ethanol-water mixture, a 10–20% propylene glycol-water mixture a naturally-occurring vegetable oil, such as sesame oil, peanut oil, cottonseed oil, and the like, or a synthetic fatty vehicle such as ethyl oleate or the like. For example, a suitable formulation for intravenous injection would be 2-3 ml of a 10–20% ethanol-water solution or a 10–20% propylene glycol-water mixture containing 100–1500 micrograms of the $\Delta^{22}$- or $\Delta^{23}$-product. Such a formulation would preferably contain 200–1000 micrograms of the $\Delta^{22}$- or $\Delta^{23}$-product of the invention. Exemplary of a suitable formulation for topical administration would be a vegetable oil solution or suspension containing 100–1500 micrograms of the $\Delta^{22}$- or $\Delta^{23}$-product. Such a formulation would preferably contain 200–1000 micrograms of a product of the invention.

The aforesaid $\Delta^{22}$- or $\Delta^{23}$-products of the invention can also be formulated for oral administration by incorporation of 100–1500 micrograms of such product into fatty acid pellets.

The subject $\Delta^{22}$- or $\Delta^{23}$-products may also be formulated for intramuscular injection by suspension of 100–1500 micrograms of such product in a vehicle such as a vegetable oil, an ethanol-water solution containing from 80–95% ethanol or a propylene glycol-water solution containing from 80–95% propylene glycol.

Buffers, preservatives, antioxidants and the like can be incorporated into the foregoing formulations as required.

As used throughout the specification and the appended claims, the term "lower alkyl" refers to a monovalent substituent consisting solely of carbon and hydrogen of from 1 to 8 carbon atoms which may be straight or branched-chain. Examples of lower alkyl groups are methyl, ethyl, n-propyl, i-propyl, tert.-butyl, hexyl, heptyl, octyl and so forth. The term "lower alkylene group" refers to a divalent substituent consisting solely of carbon and hydrogen of from 1 to 8 carbon atoms which may be straight or branched-chain and whose free valences are attached to two distinct groups. Examples of alkylene groups are methylene, ethylene, propylene and so forth. The term "lower alkoxy" refers to a lower alkyl group attached to the remainder of the molecule by oxygen. The term "aralkyl" refers to aryl lower alkyl groups such as benzyl, phenethyl and the like.

Examples of alkoxy groups are methoxy, ethoxy, isopropoxy, tert.-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, , hexanoyloxy and so forth. The term "aryl" means phenyl and substituted phenyl. The term "substituted" as applied to "phenyl" refers to phenyl which is substituted with one or more of the following groups: alkyl, halogen (i.e., fluorine, chlorine, bromine or iodine), nitro, cyano, trifluoromethyl and so forth. The term "alkanol" refers to a compound derived by protonation of the oxygen atom of an alkoxy group. Examples of alkanols are methanol, ethanol, 2-propanol, 2-methyl-2-propanol and the like. The term "alkali metal" refers to lithium, sodium and potassium.

In the formulas presented herein, the various substituents are illustrated as jointed to the steroid nucleus by one of these notations: a solid line (———) indicating a substituent which is in the $\beta$-orientation (i.e., above the plane of the molecule), a dotted line (- - - -) indicating a substituent which is in the $\alpha$-orientation (i.e., below the plane of the molecule), or a wavy line ( $\sim\!\sim$ ) indicating a substituent which may be in the $\alpha$- or $\beta$-orientation. The formulae have all been drawn to show the compounds in their absolute sterochemical configurations. Since the starting materials are derived from a naturally occurring steroid, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively.

The nomenclature adopted to define absolute configuration of substituents bound to carbon atom 24 of the steroid nucleus is described in the Journal of Organic Chemistry, 34, 2849 (1970) under the title "IUPAC Tentative Rules for the Nomenclature of Organic Chemistry. Section E. Fundamental Stereochemistry."

EXAMPLE 1

Preparation of
[1R-[1$\beta$(R*),3a$\alpha$,4$\beta$,7a$\beta$]]-1-(4-chloro-1-methyl-2-butenyl)-Octahydro-4-[[(1,1-dimethylethyl)dimethylsilyl]oxy]-7a-methyl-1H-indene (2)

A solution of 2.9 g (8.22 mmol) of [1R-[1$\beta$,[$\alpha$S*,$\beta$S*]-,3a$\alpha$,4$\beta$,7a$\beta$]]-octahydro-$\beta$,7a-dimethyl-4-[[(1,1-dimethylethyl)dimethylsilyl]oxy]-$\alpha$-ethenyl-1H-indene-1-ethanol (1) in 100 ml of anhydrous ether was cooled at 0° C. and treated dropwise and under argon with 2.76 ml (37.84 mmol) of thionyl chloride, followed by 0.276 ml of pyridine. The mixture was allowed to stir at 0° C. for 2 hours, then it was quenched by addition of 50 ml of a 2N sodium potassium tartrate solution. The ether phase was separated and the aqueous phase extracted with ethyl acetate. The combined organic phases were washed with 1N hydrochloric acid, water, 2N potassium bicarbonate solution and brine, dried (Na$_2$SO$_4$) and evaporated. The solvent evaporated in vacuo and the residue purified by rapid chromatography on silica (eluent: hexane-ethyl acetate, 19:1 (v:v)) to give 2.9 g (95% yield) of pure 2, as a low melting solid.

EXAMPLE 2

Preparation of
[1R-[1$\beta$(R*),3a$\alpha$,4$\beta$,7a$\beta$]]-1-(4-(phenylsulfonyl)-1-methyl-2-butenyl)-Octahydro-4-[[(1,1-dimethylethyl)dimethylsilyl]oxy]-7a-methyl-1H-indene (3)

A solution of 2.9 g (7.81 mmol) of the allylic chloride 2 in 130 ml of hexamethylphosphoramide was treated with 10.1 g (61.52 mmol) of benzene sulfinic acid sodium salt and stirred at room temperature under argon for 24 hours. Ice water was then added (130 ml) and, after stirring for 30 minutes, the mixture was extracted with ethyl acetate. the combined extracts were washed with water (6x), dried (Na$_2$SO$_4$), evaporated to dryness and the residue purified by rapid chromatography through silica, eluting with hexane-ethyl acetate (39:1 (v:v)) to give 3.5 g (94% yield) of pure 3, as a low melting solid.

EXAMPLE 3

Preparation of
[1R-[1β(R*),3aα,4β,7aβ]]-Octahydro-1-[6,6,6-trifluoro-5-hydroxy-5-(trifluoromethyl)-4-(phenylsulfonyl)-1-methyl-2-hexenyl]-4-[[(1,1-dimethylethyl)-dimethylsilyl]oxy]-7a-methyl-1H-indene (4)

A solution of 0.628 ml (4.48 mmol) of diisopropylamine in 10 ml of anhydrous tetrahydrofuran was cooled at 0° C. and treated dropwise under argon with 2.70 ml (4.32 mmol) of a 1.6 molar solution of n-butyllithium in hexane. After stirring for 15 minutes at 0° C., the resulting solution was cooled at −78° C. and diluted with 17 ml of anhydrous tetrahydrofuran. It was then treated dropwise with a solution of 1.25 g (2.62 mmol) of sulfone 3 in 16 ml of tetrahydrofuran and stirred at −78° C. for 30 minutes. A low stream of hexafluoroacetone was bubbled through the solution, until the yellow color discharged (5 min). After stirring for an additional 5 minutes, the reaction mixture was quenched by addition of 30 ml of a 1:1 mixture of 2N sodium potassium tartrate and 2N potassium bicarbonate solutions, allowed to come to room temperature and extracted with methylene chloride. The combined organic extracts were washed with brine, dried (Na2SO4) and evaporated to dryness. The residue was purified by fast chromatography through silica (eluent: hexane-ethyl acetate, 9:1 (v:v)) to give 1.23 g (72% yield) of 4 as a colorless oil.

EXAMPLE 4

Preparation of
[1R]1β(R*)-3aα,4β,7aβ]]-Octahydro-1-[6,6,6-trifluoro-5-hydroxy-5-(trifluoromethyl)-1-methyl-2-hexenyl]-7a-methyl-1H-inden-4-ol (5) and
[1R-[1β(R*),3aα,4β,7aβ]]-Octahydro-1-[6,6,6-trifluoro-5-hydroxy-5-(trifluoromethyl)-1-methyl-3-hexenyl]-7a-methyl-1H-inden-4-ol (6)

A solution of 1.23 g (1.91 mmol) of the sulfone 4 (epimeric mixture) in 40 ml of methanol and 40 ml of tetrahydrofuran was treated with 23 g of dipotassium hydrogen phosphate and after cooling at −20° C., with 24 g of 6% sodium amalgam. After stirring the resulting mixture for 15 minutes, 60 ml of brine was added, allowed to come to room temperature, and then extracted with ethyl acetate. The combined organic extracts were washed with brine, dried (Na2SO4) and evaporated to dryness. The residue was purified by chromatography through silica (eluting with hexane-ethyl acetate, 39:1 (v:v)) and the product (0.815 g), dissolved in 40 ml of methanol, was stirred at room temperature with 10 g of AG 50W-X4 cation exchange resin (200-400 mesh, Bio-Rad Laboratories, Richmond, CA) for 6 days. After filtration of the resin and evaporation of the solvent, the residue was purified by 2 consecutive chromatographies on silica, the first one using hexane-ethyl acetate, (9:1 (v:v)) and the second one using methylene chloride to give 200 mg of pure 5 and 50 mg of pure 6.

EXAMPLE 5

Preparation of
[1R-[1β(R*),3aα,4β,7aβ]]-Octahydro-1-[6,6,6-trifluoro-5-hydroxy-5-(trifluoromethyl)-1-methyl-2-hexenyl]-7a-methyl-1H-inden-4-one (7)

A solution of 182 mg (0.469 mmol) of diol 5 in 2 ml of methylene chloride was added to a slurry of 300 mg (1.392 mmol) of pyridinium chlorochromate in 7 ml of methylene chloride and the resulting mixture stirred at room temperature for 2.5 hours. It was then diluted with 10 ml of ether, stirred for 15 minutes, filtered with Celite® and the residue triturated several times with ether and the trituration extracts combined and filtered. Evaporation to dryness and purification of the residue by flash chromatography (eluent: hexane-ethyl acetate, 4:1 (v:v)) gave 174 mg (96% yield) of ketone 7.

EXAMPLE 6

Preparation of
[1R-[1β(R*),3aα,4β,7aβ]]-Octahydro-1-[6,6,6-trifluoro-5-(trimethylsilyloxy)-5-(trifluoromethyl)-1-methyl-2-hexenyl]-7a-methyl-1H-inden-4-one (8)

A solution of 174 mg (0.450 mmol) of ketone 7 in 9 ml of methylene chloride was treated with 0.4 ml (2.726 mmol) of trimethylsilylimidazole and stirred at room temperature, under argon for 6 hours. After addition of 1 ml of water, the mixture was stirred for an additional 20 minutes, then diluted with water and extracted with ethyl acetate. The organic extracts were washed with water and brine, dried (Na2SO4) and evaporated to dryness. The residue was purified by flash chromatography (eluting with hexane-ethyl acetate, 5:1 (v:v)) to give 177 ml (86% yield) of pure 8.

EXAMPLE 7

Preparation of
26,26,26,27,27,27-Hexafluoro-1α,25-dihydroxy-Δ$^{22}$-cholecalciferol (11)

A solution of 365 mg (0.584 mmol) of [3S-(3α,5β,Z)]-2-[2-methylene-3,5-bis[(1,1-dimethylethyl)dimethyl-silyloxy]-cyclohexylidene]ethyldiphenyl phosphine oxide in 10 ml of anhydrous tetrahydrofuran was cooled at −78° C. and treated dropwise and under argon with 0.358 ml (0.573 mmol) of a 1.6 molar solution of n-butyllithium in hexane. After stirring for 5 minutes, a solution of 177 mg (0.386 mmol) of ketone 8 in 2.5 ml of anhydrous tetrahydrofuran was added dropwise to the deep orange phosphinoxy carbanion solution and the resulting mixture stirred at −78° C. for 1 hour. It was then treated with 3 ml of a 1:1 (v:v) mixture of 2N potassium sodium tartrate and 2N potassium bicarbonate solution, allowed to come to room temperature, diluted with water and extracted with ethyl acetate. The combined organic layers were washed with brine, dried and evaporated to dryness. The residue was purified by fast filtration through silica (eluent: hexane-ethyl acetate, 20:1 (v:v)), then dissolved in 0.8 ml of methylene chloride and 9 ml of methanol and stirred at room temperature overnight with 3.5 g of AG 50W-X4 cation exchange resin. After filtration and evaporation of the solvents, the residue was dissolved in 5 ml of tetrahydrofuran and treated with 0.650 ml of a 1 molar solution of tetrabutylammonium fluoride in tetrahydrofuran and stirred for 1 hour. It was then treated with 0.5 ml of water, extracted with ethyl acetate and the combined organic phases washed with water, dried (Na2SO4) and evaporated to dryness. The crude product was purified by rapid chromatography on silica, eluting with hexane-ethyl acetate (1:2) v:v to give 181 mg (90% yield) of pure product 11, as a white amorphous powder: [α]$^{25}$D+13.9° (c 0.2 in ethanol); $^1$H NMR (400 MHz, CD3OD) 0.69 (s, 3H), 1.03 (d, J=7.2 Hz, 3H), 4.15 (br s, 1H), 4.37 (br s, 1H), 4.90 (s, 1H), 5.29 (s, 1H), 5.45 (m, 2H), 6.09 (d, J=11.2 Hz, 1H), 6.32 (d, J=11.2 Hz, 1H).

EXAMPLE 8

Preparation of
[1R,[1β(R*),3aα,4β,7aβ]]-Octahydro-1-[6,6,6-trifluoro-5-hydroxy-5-(trifluoromethyl)-1-methyl-3-hexenyl]-7a-methyl-1H-inden-4-one (9)

Following the procedure described in Example 5, 45.0 mg of [1R-[1β(R*),3aα,4β,7aβ]]-octahydro-1-[6,6,6-trifluoro-5-hydroxy-5-(trifluoromethyl)-1-methyl-3-hexenyl]-7a-methyl-1H-inden-4-ol (6) was converted to 42.0 mg of (9).

EXAMPLE 9

Preparation of
[1R-[1β(R*),3aα,4β,7aβ]]-Octahydro-1-[6,6,6-trifluoro-5-(trimethylsilyloxy)-5-(trifluoromethyl)-1-methyl-3-hexenyl]-7a-methyl-1H-inden-4-one (10)

Following the procedure described in Example 6, 42.0 mg of [1R-[1β(R*),3aα,4β,7aβ]]-octahydro-1-[6,6,6-trifluoro-5-hydroxy-5-(trifluoromethyl)-1-methyl-3-hexenyl]-7a-methyl-1H-inden-4-one (9) was converted to 35.5 mg of 10.

EXAMPLE 10

Preparation of
26,26,26,27,27,27-hexafluoro-1α,25-dihydroxy-Δ$^{23}$-cholecalciferol (12)

Following the procedure of Example 7, 35.5 mg of [1R-[1β(R*),3aα,4β,7aβ]]-octahydro-1-[6,6,6-trifluoro-5-(trimethylsilyloxy)-5-(trifluoromethyl)-1-methyl-3-hexenyl]-7a-methyl-1H-inden-4-one (10) was converted to 18.8 mg of 12 $[\alpha]_D^{25}+14.2°$ (c 0.1 in ethanol). $^1$H NMR (400 MHz, CD$_3$OD) 0.57 (s, 3H), 0.94 (d, J=7.2 Hz, 3H), 4.12 (br s, 1H), 4.35 (br s, 1H), 4.88 (s, 1H), 5.27 (s, 1H), 5.55 (d, J=15.8 Hz, 1H), 6.07 (d, J=9.6 Hz, 1H), 6.27 (m, 1H), 6.31 (d, J=9.6 Hz, 1H).

EXAMPLE 11

| Item | Ingredients | mg/capsule | | |
|---|---|---|---|---|
| 1. | 26,26,26,27,27,27-hexafluoro-1α,25-dihydroxy-Δ$^{22}$-cholecalciferol or 26,26,26,27,27,27,-hexafluoro-1α,25-dihydroxy-Δ$^{23}$-cholecalciferol | 0.00010 | 0.00025 | 0.00050 |
| 2. | polyethylene glycol 400 (PEG 400) | 200.00 | 200.00 | 200.00 |
| 3. | butylated hydroxy anisole (BHA) | 0.100 | 0.100 | 0.100 |
| 4. | ascorbyl palmitate | 1.00 | 1.00 | 1.00 |

Procedure

Dissolve items b 1, 3 and 4 in item 2, under a blanket of nitrogen and encapsulate.

EXAMPLE 12

| Item | Ingredients | | |
|---|---|---|---|
| 1. | 26,26,26,27,27,27-hexafluoro-1α,25-dihydroxy-Δ$^{22}$-cholecalciferol or 26,26,26,27,27,27-hexafluoro-1α,25-dihydroxy-Δ$^{23}$-cholecalciferol | 0.10 mg | 0.50 mg |
| 2. | 95% ethanol - 5% water | 2.00 ml | 3.00 ml |

Procedure

Dissolve item 1 in item 2 under a blanket of nitrogen and inject intramuscularly.

EXAMPLE 13

Subject: Anti-proliferative and differentiation-inducing effects of 26,26,26,27,27,27-hexafluoro-1α,25-dihydroxy-Δ$^{22}$-cholecalciferol and 26,26,26,27,27,27-hexafluoro-1α,25-dihydroxy-Δ$^{23}$-cholecalciferol.

General experimental description

Cultures of HL-60 cells were established in the absence (control) or presence of various concentrations of the test compounds. After a 4-day incubation period, the cultures were evaluated for proliferation of tumor cells, tumor cell viability, and cellular differentiation. Proliferation was assessed by directly enumerating the increased number of tumor cells resulting from incubation. Viability was determined by dye exclusion technique to learn whether any of the compounds were lethal to cultured HL-60 cells. Cellular differentiation was evaluated by determining the number of cells which had acquired the enzymes necessary to support a respiratory burst and the functional ability to phagocytose (bind/internalize) particulate material from their environment; both activities being characteristic of mature macrophages and granulocytes.

Methods

Tissue culture medium used in these experiments was RPMI-1640 supplemented prior to use to 10% v/v with fetal bovine serum (heat inactivated at 56° C. for 30 minutes), to 130 units per ml with penicillin and 130=μg per ml with streptomycin, and to an additional 1.6 millimolar with L-glutamine.

Experimental compounds were dissolved in sufficient ethanol to yield stock solutions of $1 \times 10^{-3}$ molar. Reduced lighting was employed when working with compounds and stock solutions were stored in the dark at −20° C. in an argon atmosphere. Compounds were diluted with tissue culture medium and added to flasks containing HL-60 cells to achieve the final concentrations described in each experiment.

The promyelocytic (HL-60) tumor cell line was derived from a patient with acute promyelocytic leukemia. HL-60 cells were maintained in liquid culture by serial weekly passage in tissue culture medium. In any experiment, three replicate flasks were incubated without compound (control) or in the presence of varying concentrations of compound. After 4 days of incubation at 37° C. in a humidified atmosphere of 5% CO$_2$ in air, cultures were evaluated for tumor cell proliferation, viability and differentiation.

Quantitation of proliferation was done by enumerating the number of HL-60 cells in each individual flask (3 flasks per experimental point) using a model ZBI Coulter Counter. Results are shown as the number of cells per ml of tissue culture medium expressed as the mean ± standard deviation and as percent reduction of cell number calculated according to the formula:

$$\left(1 - \frac{\text{mean number of cells in experimental cultures}}{\text{mean number of cells in control cultures}}\right) \times 100.$$

Experimental cultures with the same or slightly greater cell numbers than control cultures are reported as zero percent reduction.

Viability of tumor cells was determined by the method of trypan blue dye exclusion. Cells is tissue culture medium were added to a four-fold larger volume of 0.4% trypan blue in saline. Cells were scored as viable upon microscopic examination if they excluded dye and as dead if they were stained blue. The viability of cells from all experimental cultures was never less than that from control cultures indicating that the compounds tested were not toxic to HL-60 cells in the concentrations employed.

Quantitation of differentiated cells was done by the biochemical method of nitroblue tetrazolium (NBT) reduction. Sufficient cells were pooled from replicate cultures, centrifuged at 220×g, washed once with serum free tissue culture medium, and resuspended to $1 \times 10^6$ cells per ml in $Ca^{++}-Mg^{++}$-deficient phosphate buffered saline (prepared by supplementing $Ca^{++}-Mg^{++}$-free phosphate buffered saline (PBS) to 10% v/v with heat-inactivated fetal bovine serum). Nitroblue tetrazolium was dissolved at 1 mg per ml in $Ca^{++}-Mg^{++}$-deficient PBS with gentle heating and mixing. Tetradecanoyl phorbol acetate (TPA) was dissolved at 1 mg per ml in ethanol and stored at $-20°$ C. Just prior to use, a working solution of TPA was prepared by diluting the stock concentration 100-fold with $Ca^{++}-Mg^{++}$-deficient PBS. The test was done in $12\times75$ mm tubes by adding 0.5 ml $Ca^{++}-Mg^{++}$-deficient PBS, 1.0 ml of HL-60 cells, 0.5 ml of NBT solution, and 0.02 ml of the working TPA solution. After mixing, the tubes were incubated in a 37° C. water bath for 25 minutes then transferred to ice. Undifferentiated and differentiated cells present in any sample were determined microscopically by surveying 200–400 cells per sample. Cells without pigmented granules (clear cells) were judged to be undifferentiated while those containing greater than 3 blue-black formazan granules were scored as differentiated. Generally, differentiated cells were intensely pigmented clearly indicating the enzymatic conversion of NBT to formazan. Results are expressed as the percent of differentiated cells present in any sample as calculated according to the formula:

$$100 \times \frac{\text{number of formazan positive cells}}{\text{total number of cells counted}}.$$

Quantitation of differentiated HL-60 cells on a functional basis was done by enumerating the number of cells in any sample which had acquired the ability to phagocytose (bind/internalize) particulate material from their environment, a characteristic of mature macrophages and granulocytes. Sufficient cells were pooled from replicate cultures, centrifuged at 200×g, washed once with serum-free tissue culture medium, and resuspended to $1 \times 10^6$ cells per ml in serum-free tissue culture medium. To a 1.0 ml sample in 12×75 mm tubes was added 0.1 ml of a 1:10 (v:v) dilution from stock of fluorescent microspheres obtained as a gift from Dr. William Dreyer at the California Institute of Technology. Cells and particle were mixed, incubated for 15 minutes in a 37° C. water bath, collected in a transfer pipet, and overlayed onto a 5 ml cushion of fetal bovine serum in a 15 ml conical culture tube. After centrifugation at 150×g for 8 minutes, the excess particulate (upper layer) was discarded as was the remainder of the serum cushion leaving only a cell pellet and cell-associated particulate. The resultant pellets were resuspended in 1.0 ml of tissue culture medium containing 10% fetal bovine serum, transferred to a hemacytometer, and evaluated microscopically using both ultraviolet and visible light sources. Undifferentiated and differentiated cells present in any sample were determined microscopically by surveying 200–400 cells per sample. Non-fluorescent cells, identified only by visible light, were judged to be undifferentiated. Generally, differentiated cells were intensely fluorescent clearly indicating extensive phagocytosis of particulate material. Results are expressed as the percentage of differentiated cells present in any sample as calculated according to the formula:

$$100 \times \frac{\text{number of phagocytic cells}}{\text{total number of cells counted}}.$$

TABLE I

ANTI-PROLIFERATIVE AND DIFFERENTIATION-INDUCING EFFECTS OF 26,26,26,27,27,27-HEXAFLUORO-1α,25-DIHYDROXY-$\Delta^{22}$-CHOLECALCIFEROL ON HL-60 CELLS, IN VITRO

| Concentration of[a,b] (F)$_6$-1α,25-(OH)$_2$—$\Delta^{22}$-D$_3$ ($\times 10^{-9}$ molar) | Proliferation[c] | | Differentiation | | | |
|---|---|---|---|---|---|---|
| | HL-60 cells per ml $\times 10^{-4}$ | % reduction of cell number | NBT reduction | | phagocytosis | |
| | | | formazan "+" cells total cells counted | % "+" | phagocytic cells total cells counted | % "+" |
| Experiment 1 | | | | | | |
| None (medium control) | 77.1 ± 3.3 | — | 3/378 | <1 | not done | |
| Vehicle (0.1% ethanol) | 76.9 ± 5.1 | 0 | 2/359 | <1 | " | |
| 0.1 | 66.7 ± 1.6 | 13 | 6/347 | 2 | " | |
| 1 | 24.8 ± 0.6 | 68 | 280/328 | 85 | " | |
| 10 | 17.0 ± 1.6 | 78 | 306/319 | 96 | " | |
| 100 | 16.4 ± 1.1 | 79 | 348/356 | 98 | " | |
| Experiment 2 | | | | | | |
| None (medium control) | 92.2 ± 7.6 | — | 2/346 | <1 | 4/386 | 1 |
| Vehicle (0.1% ethanol) | 94.1 ± 3.4 | 0 | 3/381 | <1 | 3/336 | <1 |
| 0.1 | 97.9 ± 6.2 | 0 | 3/343 | <1 | 4/359 | 1 |
| 0.3 | 74.3 ± 0.8 | 21 | 45/355 | 13 | 49/376 | 13 |
| 1 | 47.6 ± 1.3 | 49 | 212/317 | 67 | 229/330 | 69 |
| 3 | 30.9 ± 1.2 | 67 | 290/316 | 92 | 284/303 | 94 |
| 10 | 28.2 ± 0.6 | 70 | 353/360 | 98 | 311/328 | 95 |
| 30 | 25.3 ± 2.0 | 73 | 310/316 | 98 | 339/344 | 98 |

TABLE I-continued

ANTI-PROLIFERATIVE AND DIFFERENTIATION-INDUCING EFFECTS OF
26,26,26,27,27,27-HEXAFLUORO-
1α,25-DIHYDROXY-Δ$^{22}$-CHOLECALCIFEROL ON HL-60 CELLS, IN VITRO

| Concentration of[a,b] (F)$_6$-1α,25-(OH)$_2$—Δ$^{22}$-D$_3$ (× $10^{-9}$ molar) | Proliferation[c] | | Differentiation | | | |
|---|---|---|---|---|---|---|
| | HL-60 cells per ml × $10^{-4}$ | % reduction of cell number | NBT reduction | | phagocytosis | |
| | | | formazan "+" cells total cells counted | % "+" | phagocytic cells total cells counted | % "+" |
| Experiment 3 | | | | | | |
| None (medium control) | 74.4 ± 1.9 | — | 2/346 | <1 | not done | |
| Vehicle (0.1% ethanol) | 80.6 ± 4.8 | 0 | 3/374 | <1 | " | |
| 0.1 | 74.4 ± 1.3 | 8 | 2/380 | <1 | " | |
| 0.3 | 60.9 ± 2.0 | 24 | 34/338 | 10 | " | |
| 1 | 38.4 ± 1.6 | 52 | 231/332 | 70 | " | |
| 3 | 24.7 ± 1.0 | 69 | 354/367 | 96 | " | |
| 10 | 21.0 ± 0.4 | 74 | 314/332 | 95 | " | |
| 30 | 21.0 ± 0.5 | 74 | 312/322 | 96 | " | |

[a]Vehicle concentration in all experimental cultures was 0.1%, v/v, ethanol.
[b](F)$_6$-1α,25-(OH)$_2$—Δ$^{22}$-D$_3$ is 26,26,26,27,27,27-hexafluoro-1α,25-dihydroxy-Δ$^{22}$-cholecalciferol.
[c]The cell viability in all cultures was greater than 95%. All cultures were initiated with 2 × $10^{-4}$ HL-6- cells per ml.

TABLE II

ANTI-PROLIFERATIVE AND DIFFERENTIATION-INDUCING EFFECTS OF
26,26,26,27,27,27-HEXAFLUORO-
1α,25-DIHYDROXY-Δ$^{23}$-CHOLECALCIFEROL ON HL-60 CELLS, IN VITRO

| Concentration of[a,b] (F)$_6$-1α,25-(OH)$_2$—Δ$^{23}$-D$_3$ (× $10^{-9}$ molar) | Proliferation[c] | | Differentiation | | | |
|---|---|---|---|---|---|---|
| | HL-60 cells per ml × $10^{-4}$ | % reduction of cell number | NBT reduction | | phagocytosis | |
| | | | formazan "+" cells total cells counted | % "+" | phagocytic cells total cells counted | % "+" |
| Experiment 1 | | | | | | |
| None (medium control) | 74.0 ± 1.0 | — | 3/318 | <1 | 11/350 | 3 |
| Vehicle (0.1% ethanol) | 67.8 ± 0.5 | 0 | 3/316 | <1 | 7/345 | 2 |
| 0.1 | 64.8 ± 1.7 | 4 | 3/310 | <1 | 4/448 | <1 |
| 0.3 | 58.8 ± 3.6 | 13 | 16/351 | 5 | 12/343 | 4 |
| 1 | 42.0 ± 2.1 | 38 | 184/328 | 56 | 155/352 | 44 |
| 3 | 22.5 ± 1.4 | 67 | 342/360 | 95 | 305/330 | 92 |
| 10 | 16.2 ± 0.7 | 76 | 353/359 | 98 | 335/347 | 97 |
| 30 | 14.5 ± 0.8 | 79 | 335/339 | 99 | 372/379 | 98 |
| 100 | 13.6 ± 0.9 | 80 | 331/335 | 99 | not done | |
| Experiment 2 | | | | | | |
| None (medium control) | 74.4 ± 1.9 | — | 2/343 | <1 | not done | |
| Vehicle (0.1% ethanol) | 80.6 ± 4.8 | 0 | 3/374 | <1 | " | |
| 0.1 | 71.4 ± 1.2 | 11 | 3/351 | <1 | " | |
| 0.3 | 64.8 ± 7.3 | 20 | 13/327 | 4 | " | |
| 1 | 55.1 ± 0.9 | 32 | 218/347 | 63 | " | |
| 3 | 47.5 ± 3.0 | 41 | 284/324 | 88 | " | |
| 10 | 44.0 ± 0.9 | 45 | 318/324 | 98 | " | |
| 30 | 39.7 ± 2.2 | 51 | 346/354 | 98 | " | |

[a]Vehicle concentration in all experimental cultures was 0.1%, v/v, ethanol.
[b](F)$_6$-1α,25-(OH)$_2$—Δ$^{23}$-D$_3$ is 26,26,26,27,27,27-hexafluoro-1α,25-dihydroxy-Δ$^{23}$-cholecalciferol.
[c]The cell viability in all cultures was greater than 95%. All cultures were initiated at 2 × $10^{-4}$ HL-60 cells per ml.

Results and Conclusion

Three experiments are shown in Table I which document that 22,23-dehydro-26,26,26,27,27,27-hexafluoro-1α,25-dihydroxycholecalciferol inhibited the proliferation of human promyelocytic tumor cells (HL-60) in vitro in a dose-dependent fashion. The lowest concentration tested (0.1×$10^{-9}$ molar) was only marginally effective while increasing concentrations inhibited the accumulation of cells. With the experimental methods employed, the maximum anti-proliferative effect was seen at concentrations of 3 to 10×$10^{-9}$ molar since the higher concentration of 30×$10^{-9}$ and 100×$10^{-9}$ molar were only slightly more effective. Cells from each of the cultures were assessed for differentiation by the method of NBT reduction in each of the experiments listed in Table I. In contrast to cells obtained from control cultures, a portion of the cells from experimental cultures reduced NBT to formazan and were thus judged to be differentiated. Moreover, the proportion of differentiated cells present in any culture was directly related to the concentration of compound present and the maximum effect was achieved at concentrations between 3 and 10×$10^{-9}$ molar Cells from experimental cultures were also judged to be differentiated by the acquisition of cellular function: the ability to phagocytose (bind/internalize) particulate material from their environment. As shown in experiment a Table I, the extent of cellular differentiation was in excellent agreement with the data produced by the NBT reduction assay. Finally, cells cultured in 0.1% ethanol as the vehicle control were not different from cells incubated in medium control cultures thus indicating that ethanol had no impact on the results seen with experimental compounds. As indicated in footnote c of Table I, the viability of cultured cells was not diminished by treatment with experimental compounds which indicates that the effects seen on HL-60 cells are mediated by non-toxic mechanisms.

Results in Table II reveal that 23,24-dehydro-26,26,26,27,27,27-hexafluoro-1α,25-dihydroxycholecalciferol exerted an anti-proliferative effect on HL-60 cells and also induced cellular differentiation by NBT analysis and evaluation of cellular function. Similar to the data in Table I, these effects were seen in the concentration ranges of $0.3-10 \times 10^{-9}$ molar, were not associated with any effects on cell viability, and were not influenced by the presence of ethanol used as a vehicle.

Taken together, these data indicate that 26,26,26,27,27,27-hexafluoro-1α,25-dihydroxy-Δ$^{22}$-cholecalciferol and 26,26,26,27,27,27-hexafluoro-1α,25-dihydroxy-Δ$^{23}$-cholecalciferol restrained the proliferation of human promyelocytic tumor cells, in vitro, even though they were not toxic to the cells. Furthermore, cells cultured in low concentrations of the compounds (0.3 to $10 \times 10^{-9}$ molar) were induced to differentiate toward a more mature cell type as evidenced by the acquisition of enzyme activity and cellular function. It is expected, then, that each of these compounds is useful as a unique approach to the management of clinical diseases which owe in part to aberrant cellular proliferation and/or differentiation. Exemplary to this issue is the management of neoplastic disease which owes to a perturbation of the normal processes of cellular differentiation.

We claim:
1. 26,26,26,27,27,27-Hexafluoro-1α,25-dihydroxy-Δ$^{22}$-cholecalciferol.
2. 26,26,26,27,27,27-Hexafluoro-1α,25-dihydroxy-Δ$^{23}$cholecalciferol.
3. A compound of the formula

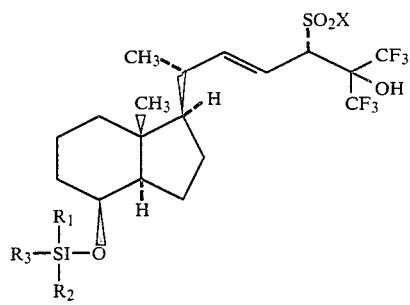

where X is aryl; and $R_1$, $R_2$ and $R_3$ each independently are lower alkyl, aryl and aralkyl.

4. A pharmaceutical composition suitable for oral administration said composition comprising a minor, effective amount of 26,26,26,27,27,27-hexafluoro-1α,25-dihydroxy-Δ$^{22}$-cholecalciferol and a major amount of a conventional pharmaceutical carrier material suitable for oral administration.

5. A pharmaceutical composition suitable for oral administration said composition comprising a minor, effective amount of 26,26,26,27,27,27-hexafluoro-1α,25-dihydroxy-Δ$^{23}$-cholecalciferol and a major amount of a conventional pharmaceutical carrier material suitable for oral administration.

6. A pharmaceutical composition suitable for parenteral administration said composition comprising a minor, effective amount of 26,26,26,27,27,27-hexafluoro-1α,25-dihydroxy-Δ$^{22}$-cholecalciferol and a major amount of a conventional pharmaceutical carrier material suitable for parenteral administration.

7. A pharmaceutical composition suitable for parenteral administration said composition comprising a minor, effective amount of 26,26,26,27,27,27-hexafluoro-1α,25-dihydroxy-Δ$^{23}$-cholecalciferol and a major amount of a conventional pharmaceutical carrier material suitable for parenteral administration.

8. A method for providing vitamin D activity to a host in need of same which method comprises administering to such host a pharmaceutical composition as set forth in claims 4, 5, 6 or 7.

9. A process for producing 26,26,26,27,27,27-hexafluoro-1α,25-dihydroxy-Δ$^{22}$-cholecalciferol which process comprises reacting a compound of the formula:

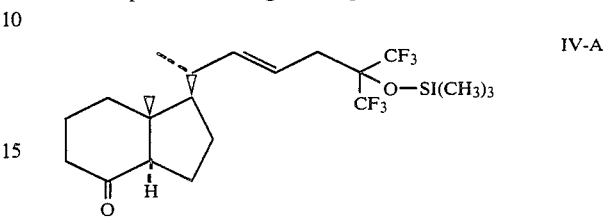

with the carbanion of [3S-(3α,5β,Z)]-2-[2-methylene-3,5-bis[(1,1-dimethylethyl)dimethylsilyloxy]cyclohexylidene]-ethyldiphenyl phosphine oxide and removing the silyl protecting groups.

10. A process for producing 26,26,26,27,27,27-hexafluoro-1α,25-dihydroxy-Δ$^{23}$-cholecalciferol which process comprises reacting a compound of the formula:

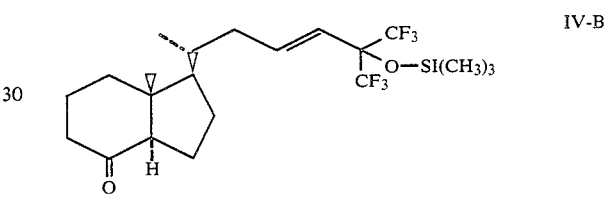

with the carbanion of [3S-(3α,5β,Z)]-2-[2-methylene-3,5-bis[1,1-dimethylethyl)dimethylsilyloxy]cyclohexylidene]-ethyldiphenyl phosphine oxide and removing the silyl protecting groups.

11. [1R-[1β(R*),3aα,4β,7aβ]]-octahydro-1-[6,6,6-trifluoro-5-(trimethylsilyloxy)-5-(trifluoromethyl)-1-methyl-2-hexenyl]-7a-methyl-1H-inden-4-one.

12. [1R-[1β(R*),3aα,4β,7aβ]]-octahydro-1-[6,6,6-trifluoro-5-(trimethylsilyloxy)-5-trifluoromethyl)-1-methyl-3-hexenyl]-7a-methyl-1H-inden-4-one.

13. A compound of the formula

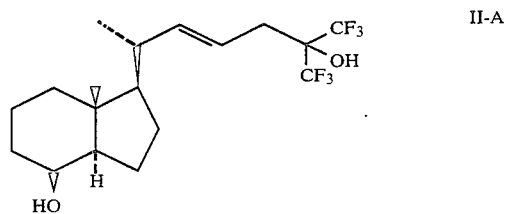

14. A compound of the formula

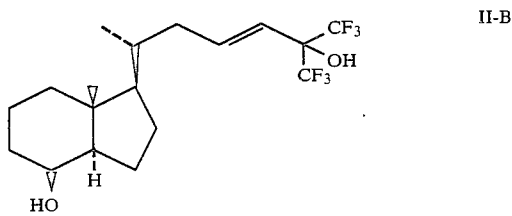

* * * * *